United States Patent
Reis et al.

(10) Patent No.: US 10,531,794 B1
(45) Date of Patent: Jan. 14, 2020

(54) PHOTOREFRACTIVE FLASH DEVICE AND SYSTEM

(71) Applicants: Alexander Reis, Eschen (LI); Werner Ganahl, Schruns (AT); Lukas Bohler, Schwarzach (AT); Frank Schaeffel, Tubingen (DE)

(72) Inventors: Alexander Reis, Eschen (LI); Werner Ganahl, Schruns (AT); Lukas Bohler, Schwarzach (AT); Frank Schaeffel, Tubingen (DE)

( * ) Notice: Subject to any disclaimer, the term of this patent is extended or adjusted under 35 U.S.C. 154(b) by 0 days.

(21) Appl. No.: 16/101,344

(22) Filed: Aug. 10, 2018

(51) Int. Cl.
| | |
|---|---|
| *G02B 26/08* | (2006.01) |
| *A61B 3/103* | (2006.01) |
| *A61B 3/14* | (2006.01) |
| *A61B 3/036* | (2006.01) |
| *A61B 3/00* | (2006.01) |

(52) U.S. Cl.
CPC .......... *A61B 3/1035* (2013.01); *A61B 3/0008* (2013.01); *A61B 3/036* (2013.01); *A61B 3/14* (2013.01)

(58) Field of Classification Search
CPC ..... A61B 3/1035; A61B 3/0008; A61B 3/036; A61B 3/14
USPC .......................................................... 359/211
See application file for complete search history.

(56) References Cited

U.S. PATENT DOCUMENTS

2016/0338587 A1* 11/2016 Gupta .................. A61B 3/1208

* cited by examiner

*Primary Examiner* — Euncha P Cherry
(74) *Attorney, Agent, or Firm* — Furr Law Firm; Jeffery Furr, Esq.

(57) ABSTRACT

The current invention is a Photorefractive Flash Device and System. It is a device that can be clipped to any portable computing device to illuminate the pupil in a way, that allows a proper pupillary reflex. On the backside of the device is a photoreceptor, on the frontside—facing the persons eyes are LEDs, centered around an opening where the lens of the camera looks through. A smartphone-app triggers the flashlight of the camera. The photoreceptor of the device senses this flash and triggers the six LEDs to flash sequentially within 200 milliseconds. 200 milliseconds is the time, the pupil needs to react. By staying under this 200 milliseconds, it can achieve high-quality pictures of the pupillary reflection, before the pupil contracts.

14 Claims, 5 Drawing Sheets

PHOTOREFRACTIVE FLASH DEVICE AND SYSTEM

CROSS-REFERENCES TO RELATED APPLICATIONS

None

FIELD OF THE INVENTION

This invention refers to the field of photorefractive flash device and method to measure and achieve high-quality pictures of the pupillary reflection.

BACKGROUND OF THE INVENTION

Ophthalmology and Optometry are health care professions concerned with the health of the eyes. Ophthalmologists, Optometrists are trained to prescribe and fit lenses to improve vision, and to diagnose and treat various eye diseases. Opticians are trained to fit lenses to improve vision.

Corrective lenses are used to correct refractive errors of the eye by bending the light entering the eye in order to alleviate the effects of conditions such as myopia, hyperopia and astigmatism.

Myopia, which is also known as nearsightedness, is where the light that comes in does not directly focus on the retina but in front of it, causing the image that one sees when looking at a distant object to be out of focus, but in focus when looking at a close object.

Hyperopia, also known as farsightedness or hypermetropia, is a defect of vision caused by an imperfection in the eye such as where the eyeball is too short or the lens cannot become round enough, causing difficulty focusing on near objects, and in extreme cases causing a sufferer to be unable to focus on objects at any distance. When an object moves toward the eye, the eye must increase its optical power to keep the image in focus on the retina. In hyperopia, the power of the cornea and lens is insufficient so the image will appear blurred.

Astigmatism is a defect of vision caused by an irregularity of the cornea or the lens in such as the curvature of the human cornea or lens is different in two main axes—like sitting on a waterball—the vertical axis is steeper than the horizontal one. In human eyes, these axis can differ, hence the degree of the steeper axis has to be detected and documented as from 0 to 179 degrees. These conditions are detected through examination and diagnosis of an eye specialist such as an Ophthalmologist, Optometrist or an Optician.

Photorefraction, invented in the 1970s, is a method to measure the refraction of an eye by analyzing the pupils red reflex using a photograph of the pupil. The core of the principle is analyzing the red reflex of an eye. Up to now, there are only two devices using this principle, both are handheld and expensive since they are infrared based. They cost up to $10,000 dollars or more making it cost prohibitive to use it as a screening device in underdeveloped countries or rural areas.

More on photorefraction is explained in the articles, Measurement of Astigmatism by automated infrared photoretinoscopy, by Florian Gekeler, Frank Schaeffel, Howard C. Howland and John Wattam-Bell, University Eye Hospital, Department of Experimental Ophthalmology, Tuebingen, Germany (FG, FS), Section of Neurobiology and Behaviour, Cornell University, Ihtaca, N.Y. (HCH), and Vision Development Unit, Department of Psychology, University College, London (JW-B). 1997 Optometry and Vision Science Vol 74, No 7, pp 472-482 and *Simulation of eccentric photorefraction images*, by Ying-Ling Chen, Bo Tan, and J. W. L. Lewis, Center for Laser Applications, The University of Tennessee Space Institute, 411 B. H. Goethert Parkway, Tullahoma, Tenn. 37388-8897, 14 Jul. 2003/Vol. 11, No. 14/*OPTICS EXPRESS* 1628 which are incorporated by reference.

All photorefractive devices currently available use infrared flashlights. But when using infrared flashlight you have to use special cameras which are able to detect infrared light. Consumer cameras like smartphone-cameras have build-in infrared-blocker to produce natural pictures. Therefore it is up to now not possible to use smartphone cameras as a photorefraction device. Furthermore the flashlight of a smartphone is positioned far away from the axis of the camera, to prevent the unwanted red reflex in portrait photos. Hence you do not get any red-reflex of the eye which is crucial in photorefraction to be analyzed.

There is a need to make the examination and diagnostics for refractive errors of the eye simpler, cheaper and easier to use as well as being portable.

There remains room for improvement in the art.

SUMMARY OF THE INVENTION

The current invention is a Photorefractive Flash Device and System. It is a device to illuminate the pupil in a way, that allows a proper pupillary reflex. By analyzing this reflex a user can calculate the refractive error of an eye.

The current invention is a device, which can be clipped on any smartphone or other such portable computing device. On the backside of the device is a photoreceptor, on the frontside—facing the persons eyes are LEDs, centered around an opening where the lens of the camera looks through.

A smartphone-app triggers the flashlight of the camera. The photoreceptor of the device senses this flash and triggers six LEDs to flash sequentially within 200 milliseconds. 200 milliseconds is the time, the pupil needs to react. By staying under this 200 milliseconds, it can achieve high-quality pictures of the pupillary reflection, before the pupil contracts. In this way, the device can use white light for the first time in the history of photorefraction.

The six LEDs are positioned in six segments. By positioning the LEDs in this way, it is not only possible to calculate the spheric error of an eye (myopia and hyperopia). It is also possible to calculate the power of an astigmatism and the axis of an astigmatism.

The software, which triggers the camera flash is taking pictures of the eye, in each moment one of the six LEDs is lighting up.

BRIEF DESCRIPTION OF DRAWINGS

Without restricting the full scope of this invention, the preferred form of this invention is illustrated in the following drawings in which.

DETAILED DESCRIPTION OF THE PREFERRED EMBODIMENT

There are a number of significant design features and improvements incorporated within the invention. The current invention is a Photorefractive Flash Device and System.

While Photorefraction was invented in the 1970s, and is a method to measure the refraction of an eye by analyzing the pupils red reflex using a photograph of the pupil, prior to the current invention there were only two devices using this method. Both are handheld and expensive and are infrared base. The current invention is a device and method to transfer this principle to any handheld-device 10, such as a smartphone, tablet or laptop computer. This method can be used with any device with a camera and a microprocessor or web connection.

Figure 1:
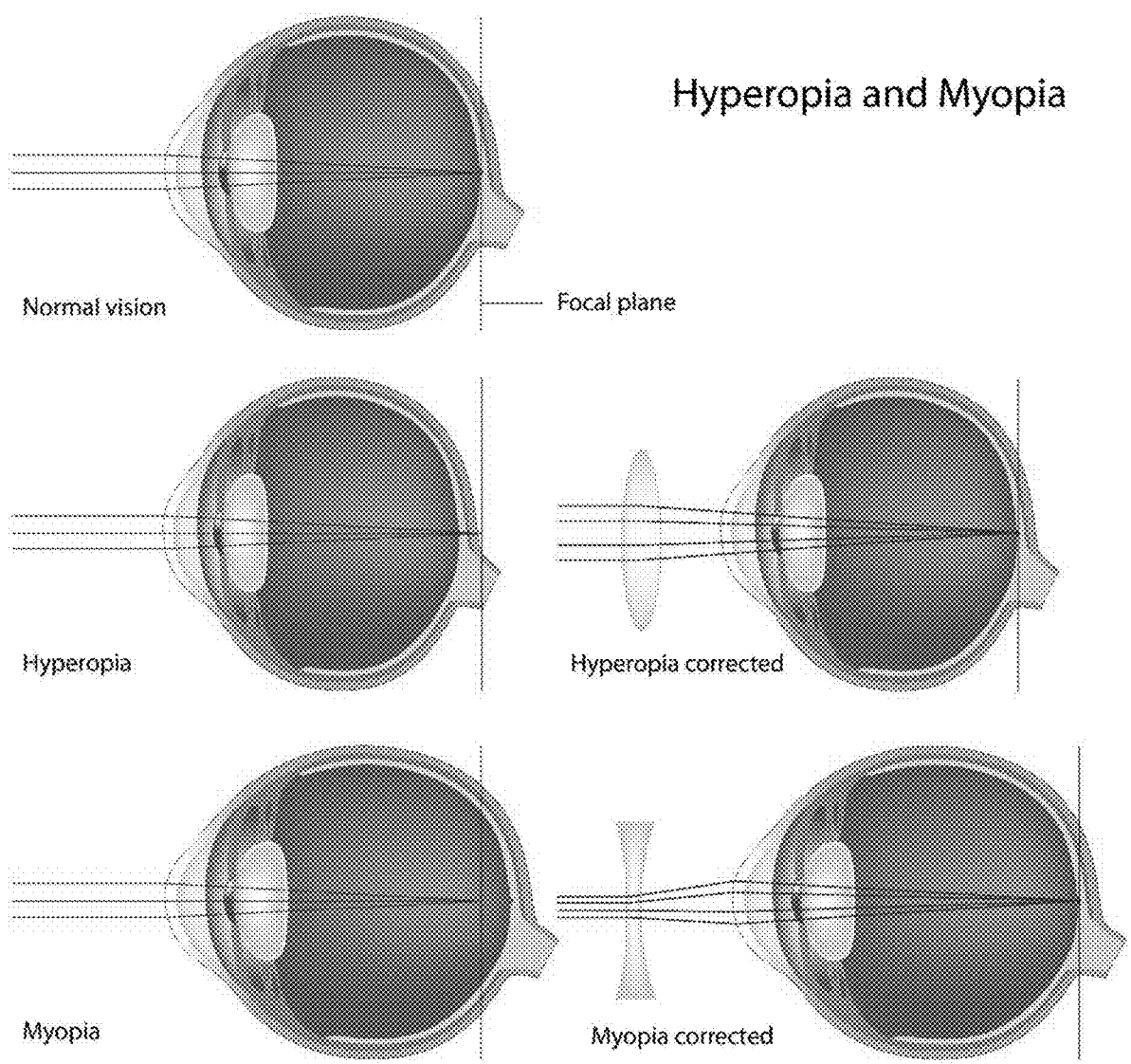
FIG. 1 shows the conditions such as myopia and hypermetropia.

Some of the main defects being examined for are conditions such as myopia, hyperopia and astigmatism. These conditions are shown in FIG. 1.

Myopia is where the light that comes in does not directly focus on the retina but in front of it, causing the image that one sees when looking at a distant object to be out of focus, but in focus when looking at a close object.

Hyperopia is a defect of vision caused by an imperfection in the eye such as where the eyeball is too short or the lens cannot become round enough, causing difficulty focusing on near objects, and in extreme cases causing a sufferer to be unable to focus on objects at any distance.

Photorefraction can be used for the detection of specific vision problems. The preferred embodiment is off-axis, or eccentric, photorefraction for which an image of the subject's pupil is obtained using a device 1 that affixes to a smart phone 10, tablet or similar device (such as a laptop), that is aligned eccentric to a flash-lamp illumination source. The geometric form and irradiance of pupil image will be dependent upon the subject's pupil size, refractive errors, staring angle, other properties of the eye, and the design parameters of the optical measurement system.

Figure 2:
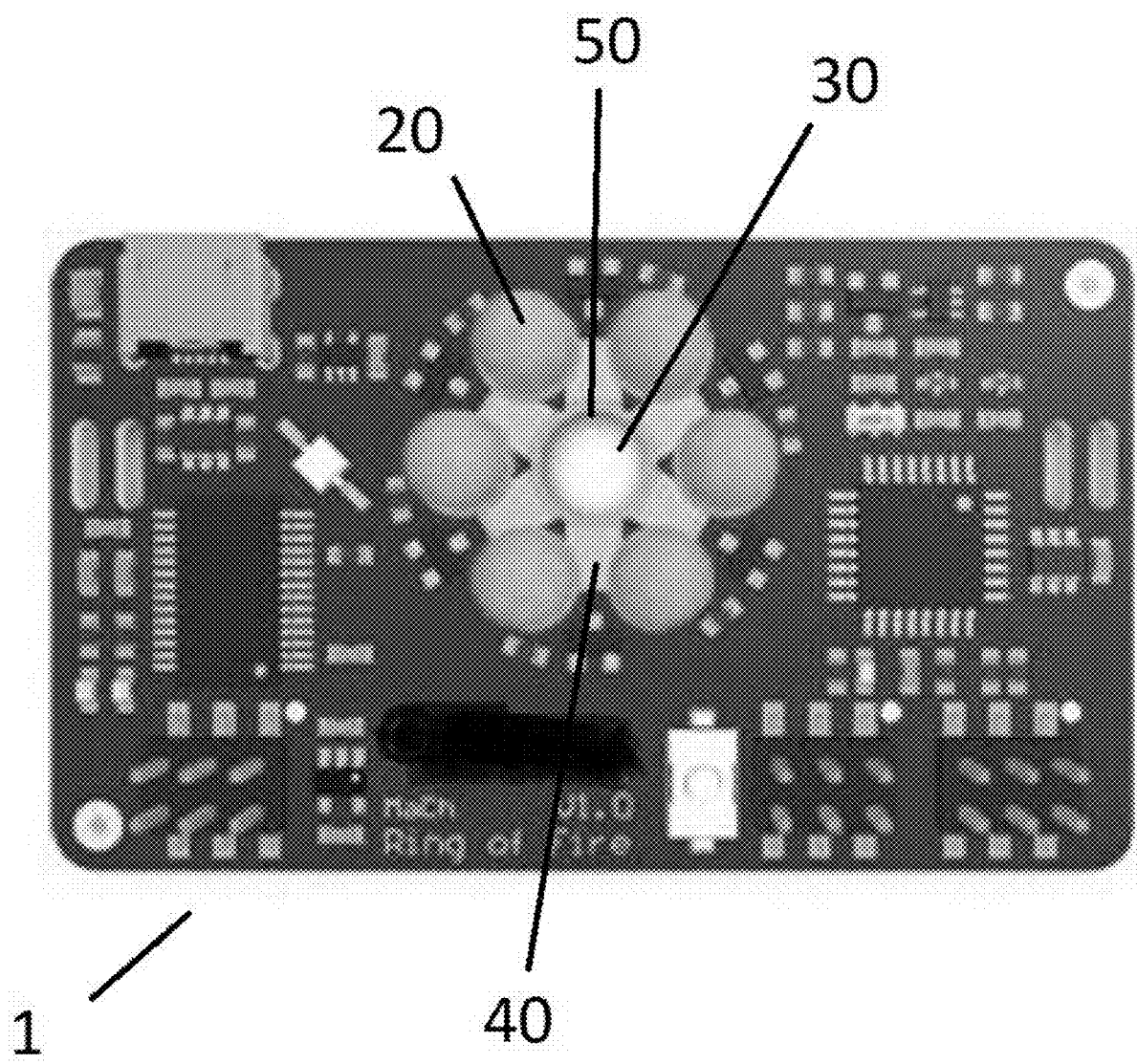
FIG. 2 shows the photoreceptor device.
Figure 3:
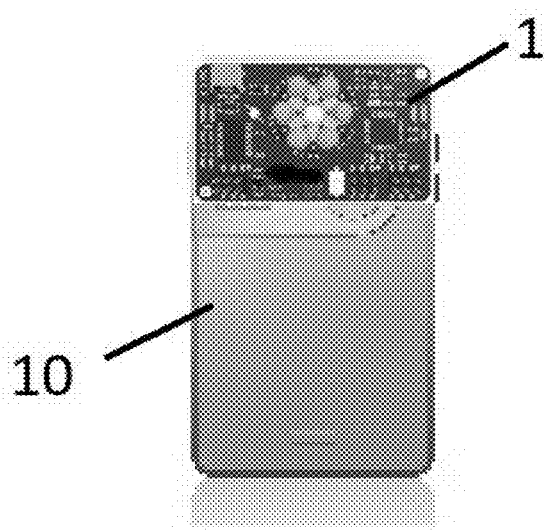
FIG. 3 shows the photoreceptor device on a smart phone.
Figure 4:
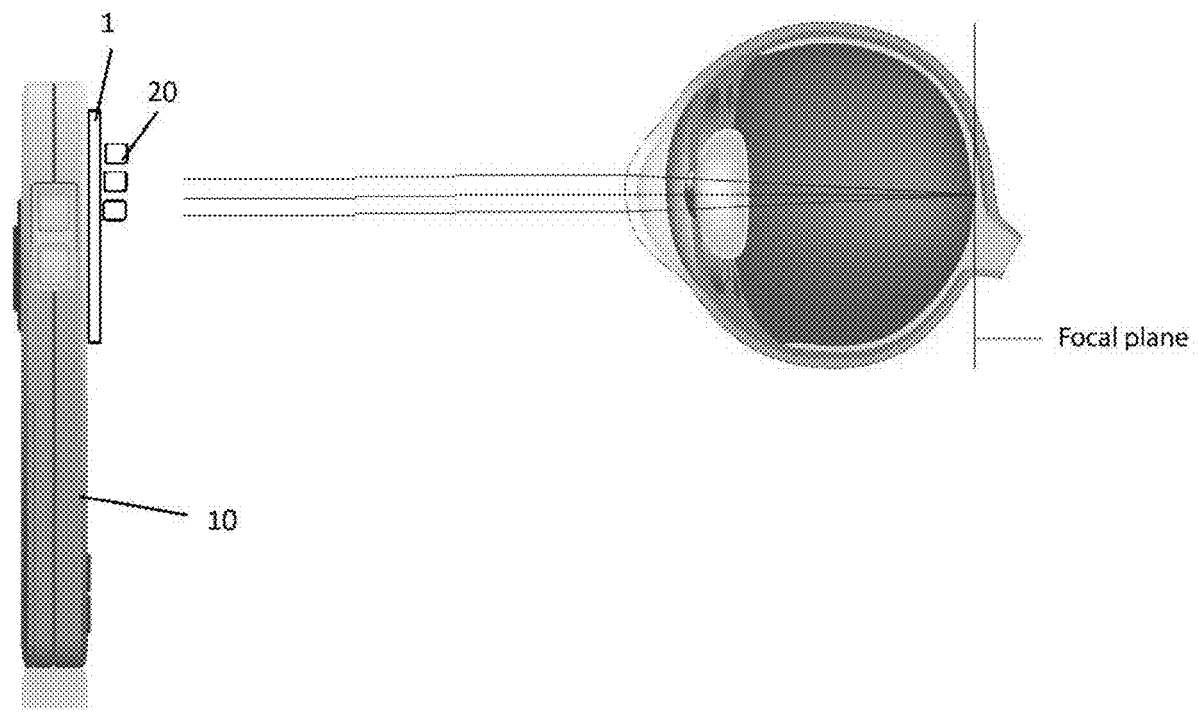
FIG. 4 shows the photoreceptor device being used.

The current invention will use photorefractive effects on the eye to measure and diagnose whether or not the eyes are myopic, hyperopic or astigmatic, as well as other issues with the eyes that may require corrective measures using a device 1, as shown in FIG. 2, that attaches to a hand held or mobile device 10 such as a cell phone, tablet or laptop as shown in FIG. 3.

As shown in FIG. 2, the basic optical concept of photorefraction is that the light rays from the device enter the eye, are reflected from the retina, and are then collected by the camera 30 of the smartphone 10. With a properly functioning eye, the light rays from the far zone are imaged onto the retina into the smallest size. The reflected (or scattered) light rays from the retina are then focused by the eye in the second pass and form a converging cone for myopic or diverging cone if hyperopic, symmetric to the axis that connects the eye and light source. Normally, the signal light cone from an emmetropic eye has the smallest solid angle. The solid angle of the reflection light cone increases with the degree of refractive error.

The flashlight of a smartphone is too far away from the axis of the camera, hence you do not get any proper red-reflex of the eye which could be analyzed.

The device 1, which can be clipped on any smartphone 10 or similar device. On the backside of the device 1 is a photoreceptor 40, on the frontside—facing the persons eyes are a light source which in the preferred embodiment are six LEDs 20 that are centered around an opening 50 where the lens of the camera 30 looks through.

The device 1 works with a smartphone application. The application, data and processing code can reside in the non-transitory memory of one or more computing devices. The application in the preferred embodiment would be written to act like a smart phone application (app). The application triggers the flashlight 60 of the camera 30. The photoreceptor 40 of the device lenses this flash and triggers the LEDs 20, six in the preferred embodiment, to flash sequentially within 200 milliseconds. 200 milliseconds is the time, the pupil needs to react. By staying under this 200 milliseconds, the device 1 achieves high-quality pictures of the pupillary reflection, before the pupil contracts. In this way, the device 1 can use white light for the first time in the history of photorefraction.

The LEDs 20 are positioned in six segments. By positioning the LEDs 20 in this way, it is not only possible to calculate the spheric error of an eye (myopia and hyperopia). It is also possible to calculate the power of an astigmatism and the axis of an astigmatism. The application triggers the camera flash and takes pictures of the eye, in each moment one of the six LEDs 20 is lighting up. The application will measure the spherical aberration, the anisotropic scattering function of the retina, multiple scattering in the retinal tissue and the non-circular shape of the pupil.

Operations

The current invention can be used for measurement of refraction from a distance of about 80 cm. The setup is simple: it consists of a device 1 attached to smart phone 10, camera, laptop, tablet or similar device focused to the subject's pupils.

For a measurement of astigmatic refractions (sphere, cylinder, angle of cylinder axis) at least 2 or 3 measurements with different orientations of the light source are necessary to be performed.

The device 1 which uses a program or an application (app) will measure the spherical aberration, the anisotropic scattering function of the retina, multiple scattering in the retinal tissue and the non-circular shape of the pupil.

The device 1 will be easy to position properly given its small size and portable nature. The device 10 will record the photorefractive effects of the eyes. Both are being measured simultaneously, hence reducing the examination time, which is of great advantage when used as a screening device in small children. It will record this information as data.

Figure 5:
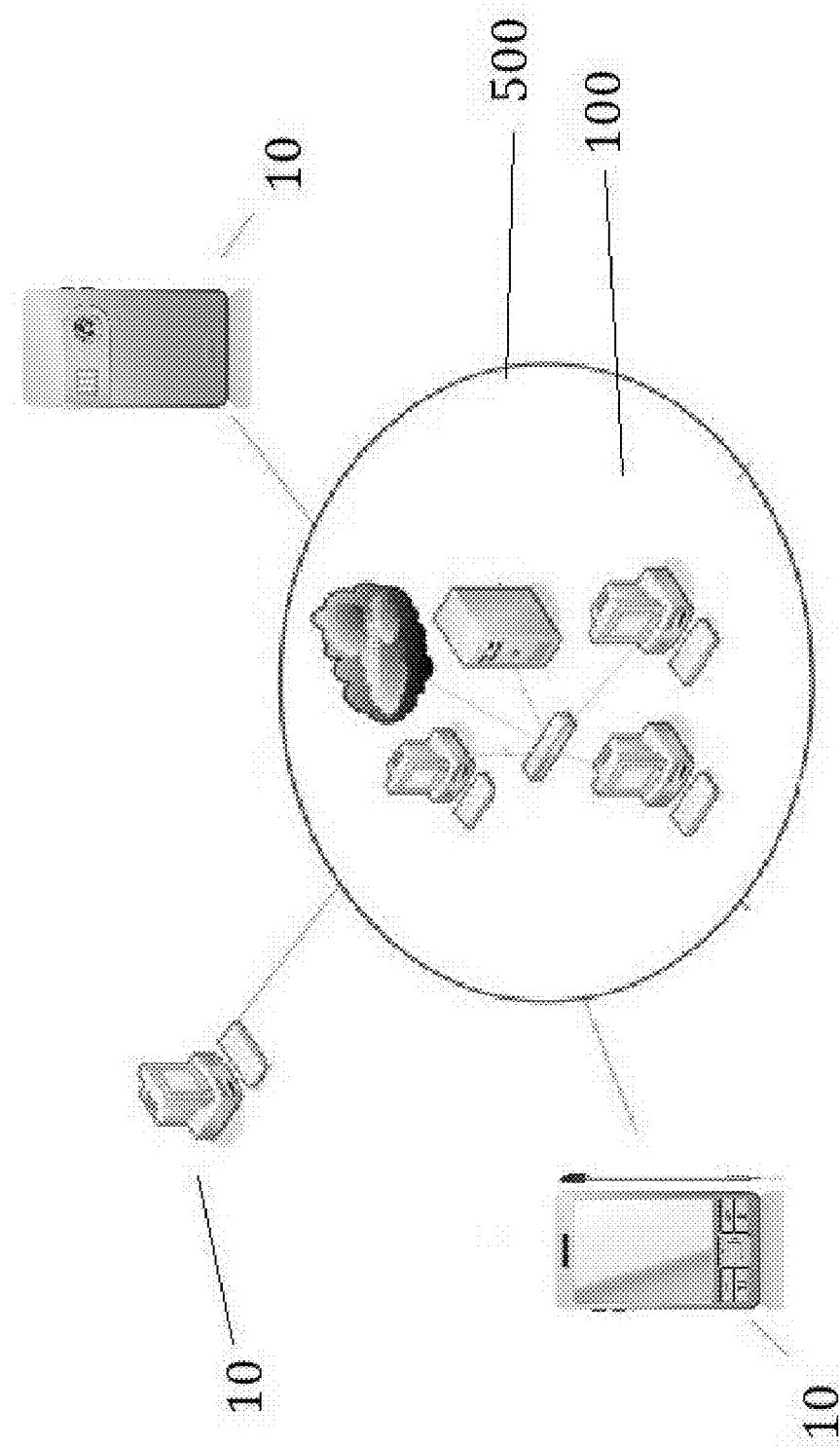
FIG. 5 shows multiple devices being connected to a server.

The device 1 can use the measurement to calculate the findings itself using diagnostic software or application (app) if it has computing means such as a microprocessor with memory or it could be connected and upload the data to a server or servers 500 that have software 100 stored and run on electronic memory to analyze the results of the eye measurement to determine the findings. As shown in FIG. 5 multiple devices can be connected and transmit and receive data from the server 500. The server 500 can even be a world away in cases where the diagnostics are being done in $3^{rd}$ world countries.

The current invention uses the device 1 with smart algorithms to analyze the pictures taken by any portable device 10 with a camera 30. This is novel and new to the art.

ADVANTAGES

The Inventor has created a system that can be used anywhere to efficiently and economically measure for and detect refractive error of the eye. This system will vastly increase the ability to perform and diagnose eye defects, especially in poorer regions of the world. It will also give health care providers such as pediatricians, kindergarten-teachers or social workers an unexpensive and easy to use screening device.

All description giving is for clarification purposes only, and not intended to limit the invention features and embodiment measurements. Further aspects of the invention will become clear from consideration of the drawings and the ensuing description of the preferred embodiments. A person skilled in the art will realize that other embodiments of the invention can vary and the details of the invention can be modified in a number of respects, all without departing from the inventive concept. Thus, the following drawings and descriptions are to be regarded as illustrative in nature and not restrictive.

With respect to the above description, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur by those skilled in the art, it is not desired to limit the invention to the exact construction and operation shown and described, and accordingly, all suitable modifications and equivalents may be resorted to, falling within the scope of the invention.

We claim:

1. A device to examine eyes comprising:
    having a front side and a back side and having a plurality of light sources being on the front side positioned around an opening with photoreceptor where the photoreceptor is on the back side where the light sources flash sequentially within 200 millisecond producing a pupillary reflection and where the device uses a camera to take pictures of the pupillary reflection using the photorefractive effects to analyze the optical, refractive error of an eye.

2. The device according to claim 1 where the light source is a plurality of LEDS.

3. The device according to claim 2 where there are six LEDs evenly space around the opening.

4. The device according to claim 1 where the device is clipped on a smartphone.

5. The device according to claim 1 where the device connects to a smartphone application where the application, data and processing code can reside in the non-transitory memory where the application triggers a flashlight of a camera of the smartphone where the photoreceptor of the device senses this flash and triggers the light sources.

6. The device according to claim 1 where the device does not use a lens.

7. The system according to claim 6 where the system does not use a lens.

8. The device according to claim 1 where the taken pictures are sequenced with the light sources flashes.

9. The system according to claim 6 where the taken pictures are sequenced with the light sources flashes.

10. A system to examine eyes comprising:
    using a device having a front side and a back side and having a plurality of light sources being on the front side positioned around an opening with photoreceptor where the photoreceptor is on the back side where the light sources flash sequentially within 200 millisecond producing a pupillary reflection where the device uses a camera to take pictures of the pupillary reflection and using the photorefractive effects to analyze the optical, refractive error of an eye.

11. The system according to claim 10 where the light source is a plurality of LEDS.

12. The system according to claim 11 where there are six LEDs evenly space around the opening.

13. The system according to claim 10 where the device is clipped on a smartphone.

14. The system according to claim 10 where the device connects to a smartphone application where the application, data and processing code can reside in the non-transitory memory where the application triggers a flashlight of a camera of the smartphone and where the photoreceptor of the device senses this flash and triggers the light sources where the light sources flash sequentially within 200 milliseconds and use the camera to take pictures of the pupillary reflection.

* * * * *